(12) United States Patent
Stalcup et al.

(10) Patent No.: US 10,772,731 B2
(45) Date of Patent: Sep. 15, 2020

(54) ORTHOPAEDIC IMPLANT WITH BONDED POROUS MATERIAL

(71) Applicant: SMed-TA/TD, LLC, Columbia City, IN (US)

(72) Inventors: Gregory C. Stalcup, Fort Wayne, IN (US); Paul S. Nebosky, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 42 days.

(21) Appl. No.: 15/949,700

(22) Filed: Apr. 10, 2018

(65) Prior Publication Data

US 2018/0296349 A1 Oct. 18, 2018

Related U.S. Application Data

(60) Provisional application No. 62/485,610, filed on Apr. 14, 2017.

(51) Int. Cl.
*A61F 2/30* (2006.01)
*A61F 2/38* (2006.01)
*B29C 65/54* (2006.01)
*B29C 65/00* (2006.01)
*B29L 31/00* (2006.01)

(52) U.S. Cl.
CPC ...... *A61F 2/30771* (2013.01); *A61F 2/30749* (2013.01); *A61F 2/30767* (2013.01); *A61F 2/3859* (2013.01); *B29C 65/542* (2013.01); *B29C 66/727* (2013.01); *A61F 2/3094* (2013.01); *A61F 2002/30011* (2013.01); *A61F 2002/3092* (2013.01); *A61F 2002/3093* (2013.01); *A61F 2002/30677* (2013.01); *A61F 2002/30784* (2013.01); *A61F 2002/30827* (2013.01); *A61F 2002/3863* (2013.01); *A61F 2310/00029* (2013.01); *B29L 2031/753* (2013.01)

(58) Field of Classification Search
CPC .. A61F 2/28; A61F 2/38; A61F 2/3859; A61F 2/30771; A61F 2/30749
See application file for complete search history.

(56) References Cited

U.S. PATENT DOCUMENTS

2013/0304227 A1\* 11/2013 Hawkins ............. A61F 2/30771
623/23.5

\* cited by examiner

*Primary Examiner* — Jason-Dennis N Stewart
(74) *Attorney, Agent, or Firm* — Taylor IP, P.C.

(57) ABSTRACT

An orthopaedic implant includes a main body having a surface with at least one bonding feature, at least one porous material having a plurality of pores, and a bonding material placed in the plurality of pores of the at least one porous material and the at least one bonding feature to form a bond between the at least one porous material and the main body.

20 Claims, 5 Drawing Sheets

ORTHOPAEDIC IMPLANT WITH BONDED POROUS MATERIAL

CROSS REFERENCE TO RELATED APPLICATIONS

This is a non-provisional application based upon U.S. provisional patent application Ser. No. 62/485,610, entitled "ORTHOPAEDIC IMPLANT WITH BONDED POROUS MATERIAL," filed Apr. 14, 2017, which is incorporated herein by reference.

FIELD OF THE INVENTION

The present invention relates to orthopaedic implants and, more particularly, to orthopaedic implants configured for secure implantation, and the manufacture thereof.

BACKGROUND OF THE INVENTION

Conventional orthopaedic implants are typically secured to tissue at the implantation site via known orthopaedic fastening devices, such as bone screws and/or pins. Some orthopaedic implants contain ingrowth material that provide additional means for securing the implant to the surrounding tissue via tissue growth into the ingrowth material. Although implants secured in such a manner typically do not become loose from the implantation site, adjustment or even separation of components of the implant, for example, between the ingrowth material and the body of the implant, may occur, thereby causing the implant to become reoriented with respect to the implantation site, or causing components of the implant to become loose or even unattached from the implantation site, leading to failure of the implant to function properly.

What is needed in the art is an orthopaedic implant, and a method of manufacture thereof, that can overcome some of the previously described disadvantages of known orthopaedic implants.

SUMMARY OF THE INVENTION

In accordance with an aspect of the present invention, there is provided an orthopaedic implant including a main body having a surface with at least one bonding feature, at least one porous material having a plurality of pores, and a bonding material placed in the plurality of pores of the at least one porous material and the at least one bonding feature to form a bond between the at least one porous material and the main body.

In accordance with another aspect of the present invention, there is provided a method of forming an orthopaedic implant including providing an implant having a surface with at least one bonding feature, placing a porous material having a plurality of pores against the surface, and flowing a bonding material into the at least one bonding feature and the plurality of pores to bond the porous material to the implant.

BRIEF DESCRIPTION OF THE DRAWINGS

The above-mentioned and other features and advantages of this invention, and the manner of attaining them, will become more apparent and the invention will be better understood by reference to the following description of exemplary embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DESCRIPTION OF THE INVENTION

Figure 1:
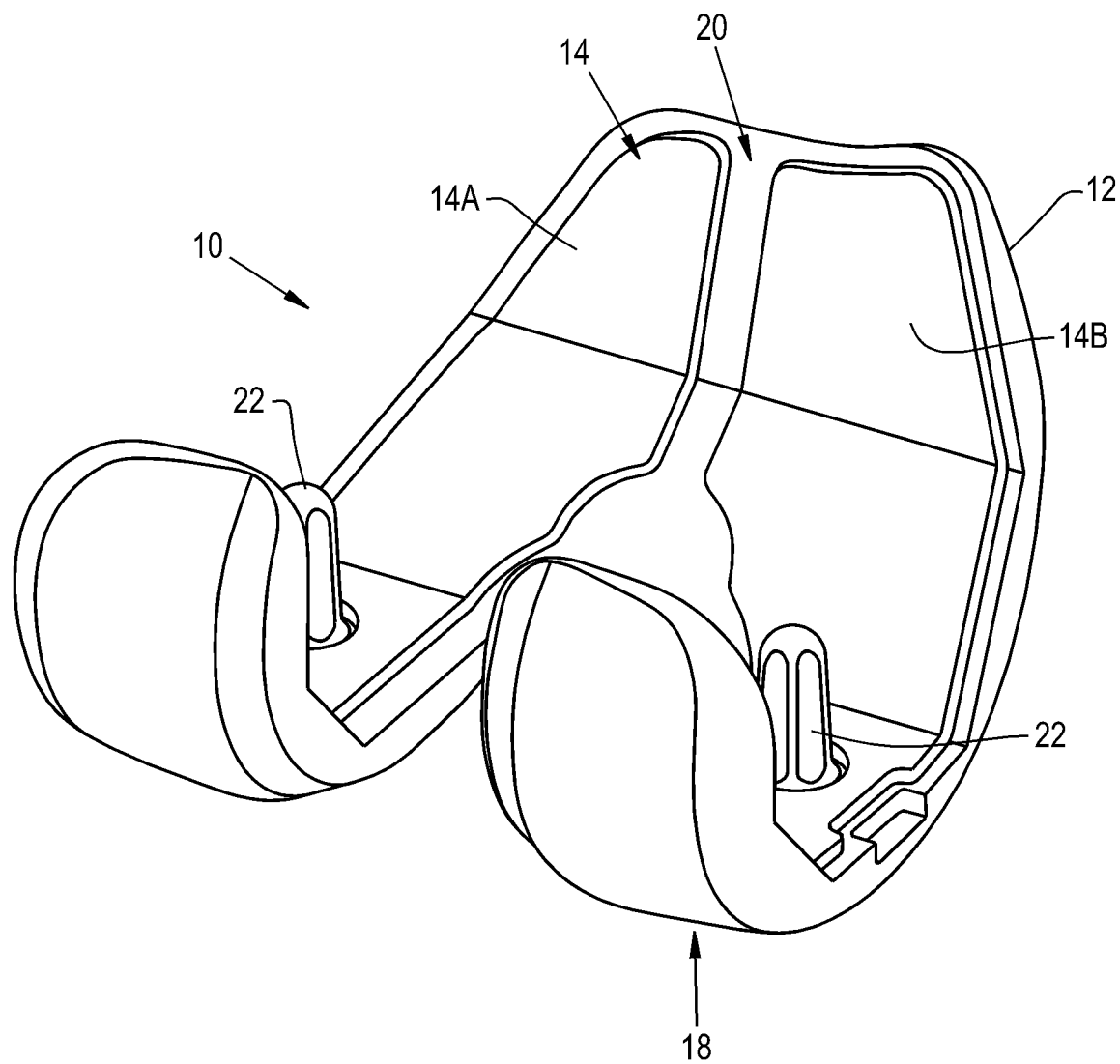
FIG. 1 is a perspective view of an orthopaedic implant configured for implantation within a body, in accordance with an embodiment of the present invention.

Referring now to the drawings, and more particularly to FIGS. 1-5, there is shown an embodiment of an orthopaedic implant 10 configured for implantation within a body of a patient which generally includes an implant main body 12 and a porous ingrowth material 14 bonded to the main body 12 by a bonding material 16.

Figure 2:
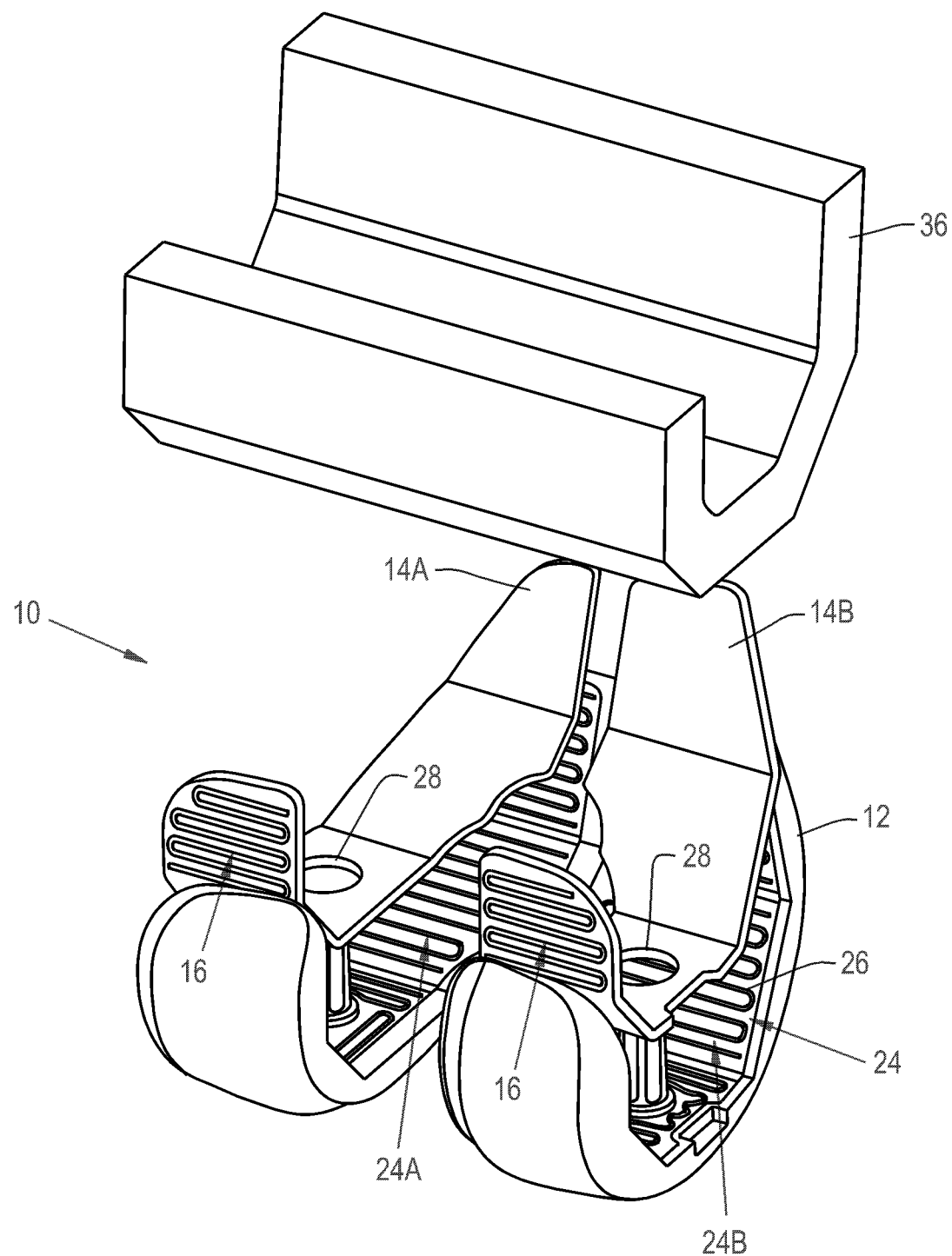
FIG. 2 is a perspective view of an orthopaedic implant of FIG. 1 and an induction heater for use with the orthopaedic implant, in accordance with an embodiment of the present invention.
Figure 4:
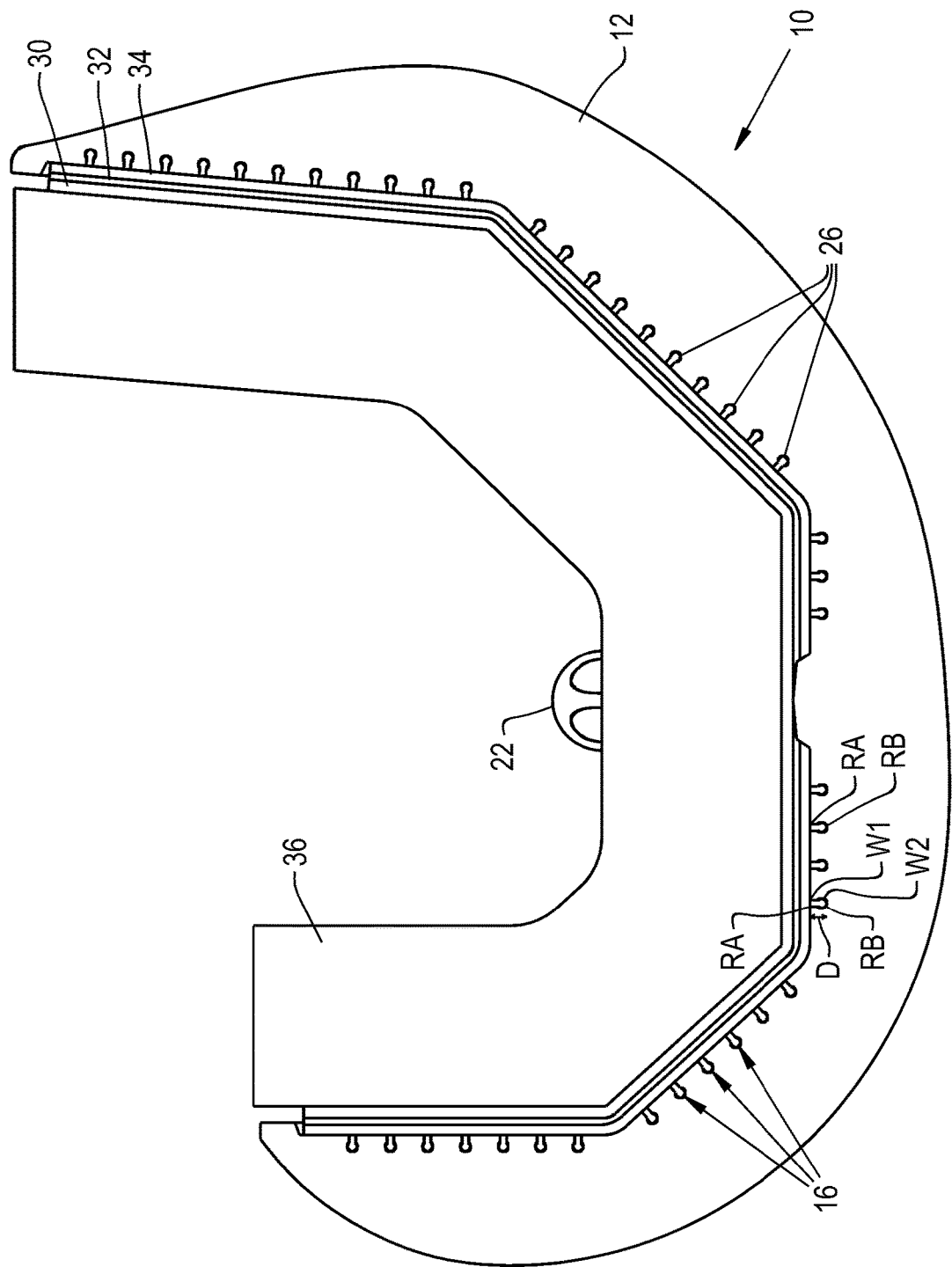
FIG. 4 is a cross-sectional view of the orthopaedic implant combined with the induction heater of FIG. 3, in accordance with an embodiment of the present invention.
Figure 5:
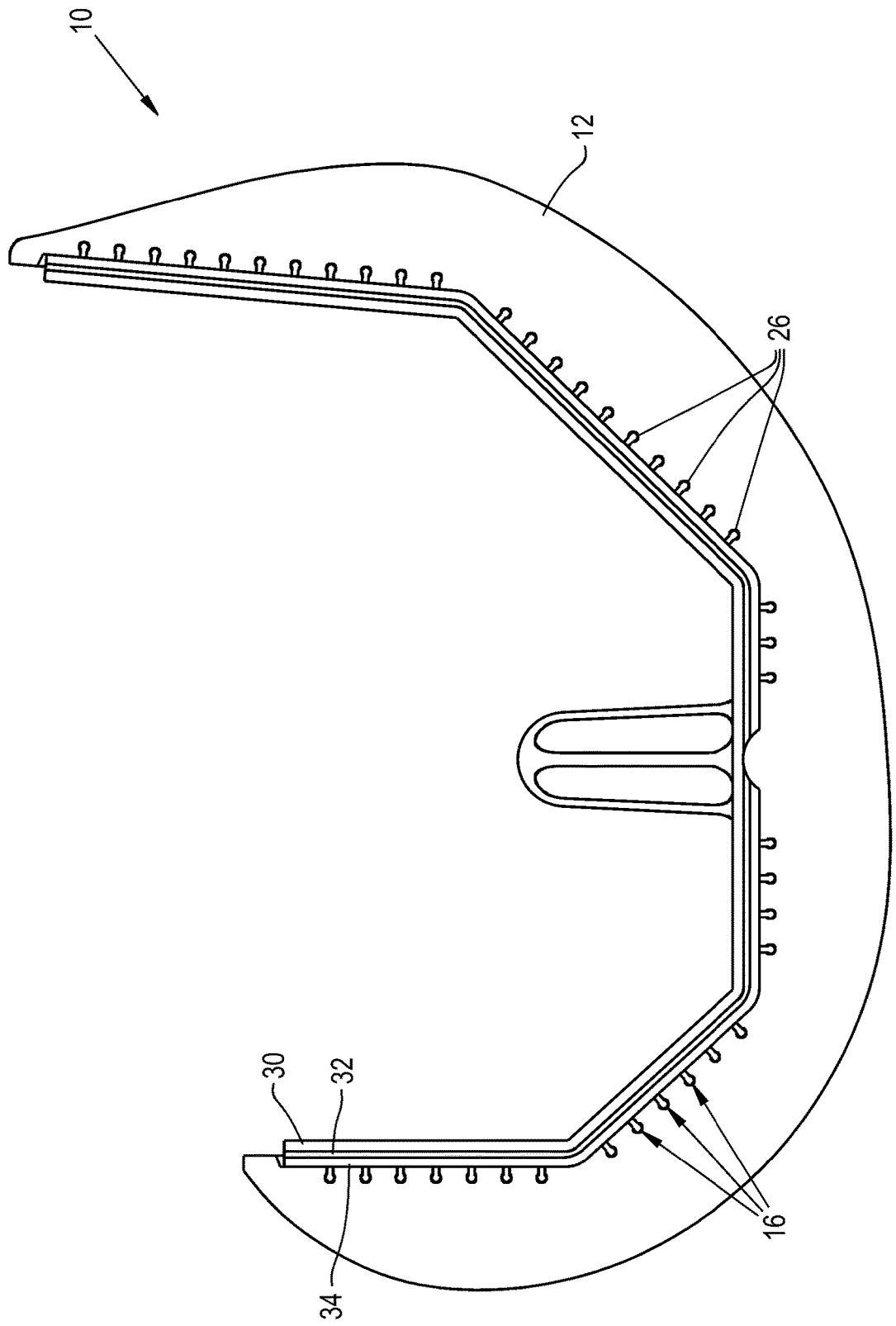
FIG. 5 is a cross-sectional view of the orthopaedic implant of FIG. 1, in accordance with an embodiment of the present invention.

The main body 12 of the orthopaedic implant 10 is shown to be in the form of a femoral knee implant which is configured for implantation in a femur, but it should be appreciated that the main body 12 can be formed in different shape corresponding to other anatomical features. The main body 12 of the knee implant 10 includes two condylar portions configured for facilitating the articulation of the knee. The main body 12 has an articulating surface 18 for articulating against a head of a tibia and an engagement surface 20 for engaging a resected femur. The engagement surface 20 includes two protrusions 22, shown as solid posts, extending outwardly therefrom and at least one bonding feature 24. As shown in FIG. 2, the engagement surface 20 has two sets of bonding features 24A, 24B. The bonding features 24A, 24B may each include grooves, slots, and/or bores that help the porous ingrowth material 14 bond to the main body 12, which will be described further herein. The bonding features 24A, 24B are respectively shown as a first and a second pattern of grooves 26 that extend the lengths of the main body 12 in a sinusoidal pattern. However, it should be appreciated that the bonding features 24A, 24B may partially extend across the width and length of the engagement surface 20 and may include any configuration or pattern of laterally and/or longitudinally displaced lines and/or curves. As shown in FIGS. 4-5, the bonding features 24A, 24B can be formed with a depth D into the engagement surface 20 and have a plurality of dimensions, such as a first width W1 and a second width W2, which are not the same at different regions RA, RB of the bonding features 24A, 24B relative to the depth D. For example, the bonding features 24A, 24B can have the first region RA with first width W1 closer to the engagement surface 20 and the second region RB with the second width W2, which is greater than the first width W1, further from the engagement surface 20. The significance of these differing dimensions W1 and W2 will be discussed further herein.

The main body 12 of the knee implant 10 comprises one or more biocompatible materials suitable for short or long-term placement within an animal body, human or otherwise. In one exemplary embodiment, the main body 12 comprises Co—Cr; however, the main body 12 may comprise other biocompatible materials including but not limited to: metals such as titanium, stainless steel, and/or tantalum; polymers such as ultra-high molecular weight polyethylene (UHM-WPE), other forms of polyethylene, polyaryl ether ketones (PAEK) such as polyether ether ketone (PEEK), polylactic acid (PLA), and/or polyglycolic acid (PGA); and/or ceramics such as hydroxyapatite (HA), high-density alumina, so-called "Bioglass," and graphite. It should be appreciated that all of the previously mentioned materials are exemplary only, and many other types of biomaterials can be incorporated in the main body 12 according to the present invention.

The porous material 14 can include a first and a second porous material 14A, 14B that are respectively bonded to the bonding features 24A, 24B. The first and second porous materials 14A, 14B have respective holes 28 for allowing the passage of the protrusions 22 therethrough. The shape of the porous materials 14A, 14B may respectively correspond to the shape of the engagement surface 20 with the bonding features 24A, 24B such that the porous materials 14A, 14B substantially cover the bonding features 24A, 24B. The porous materials 14A, 14B may also be configured to only partially cover the bonding features 24A, 24B of the main body 12 or the porous materials 14A, 14B may cover the entire engagement surface 20 of the main body 12, depending on the desired amount of tissue ingrowth. It should be appreciated that the porous material 14 may be composed of a single member or of multi-sectional members, having two, three, four, or more porous materials that respectively bond to the bonding features 24A, 24B. As shown in FIGS. 4-5, the porous material 14 can include one or more first porous layers 30 defining an outer surface of the porous material 14, a non-porous layer 32, and one or more second porous layers 34 abutting against the engagement surface 20 of the main body 12. For ease of description, the first porous layer(s) 30 will be described as only a single first porous layer 30 and the second porous layer(s) 34 will be described as only a single second porous layer 34, but it should be appreciated the first porous layer 30 and/or second porous layer 34 can be formed of multiple layers bonded together. The first porous layer 30 may be in the form of a porous ingrowth material having numerous pores in order to interface with existing bone material during implantation of the implant 10 and allow tissue ingrowth into the first porous layer 30 following implantation. The non-porous layer 32 can be situated in between the first and second porous layers 30, 34, and act as a material barrier between the first and second porous layers 30, 34. The second porous layer 34 may be in the form of a porous material having numerous pores to facilitate bonding with the bonding features 24A, 24B of the main body 12 with the bonding material 16. For example, the pores of the second porous layer 34 may be interconnected with one another throughout the second porous layer 34 and at least partially filled with the bonding material 16. In this sense, it should be appreciated that the porosity and/or pore shape and distribution of the first porous layer 30 and second porous layer 34 may be different from one another. The first and second porous layers 30, 34 are shown to have different pore patterns and the first porous layer 30 has a greater thickness than the second porous layer 34. However, the first and second porous layers 30, 34 may have identical pore patterns and the thickness of the second porous layer 34 may be equal to or greater than the thickness of the first porous layer 30.

The porous material 14 may have one or more layers of porous and/or non-porous materials, for example, two, three, or four or more layers of porous and/or non-porous materials that are bonded together with each bonded porous layer having a pore pattern formed therein. The pore patterns may or may not be identical throughout the multiple layers of the porous material 14. The pores can be formed in the porous material 14, or each individual layer of the porous material 14, by any suitable method, such as laser cutting, chemical etching, and punching. The porous material 14 may be formed, for example, of beads, mesh, lattice, etc.

The porous material 14 may comprise any suitable biocompatible bone ingrowth or on-growth surface such as OSTEOSYNC™, Beads, Plasma Spray, or other similar bone or tissue ingrowth or on-growth material. Exemplary materials include porous polymer materials including polyetheretherketone (PEEK), polymer scaffolds, allograft bone, autograft bone, easily cut metal scaffold, or other similar bone or tissue ingrowth surfaces. Such ingrowth materials are known and can include, but are not limited to, various porous metals, polymers, and/or ceramics. Additionally, if the ingrowth material is porous, the pores of the material which will contact bone tissue, i.e., the first porous layer 30, can be filled with one or more bioactive substances to further encourage bone ingrowth such as growth factors, anti-inflammatories, antibiotics, painkillers, etc. It should therefore be appreciated that any ingrowth material attached to the engagement surface 20 of the main body 12 of the orthopaedic implant 10 can be tailored to achieve specific design criteria and be utilized according to the present invention.

Referring now specifically to FIG. 2, there is shown the bonding material 16 that is configured for bonding the porous material 14 to the main body 12. The bonding material 16 can be placed in the pores of the second porous layer 34 of the porous material 14, and can be placed in the bonding features 24A, 24B of the main body 12 to form a bond between the porous material 14 and the main body 12. For example, the bonding material 16 may be initially affixed to the second porous layer 34 of the porous material 14, as shown, by melting or otherwise flowing a portion of the bonding material 16 into the pores of the second porous layer 34. However, it should be appreciated that the bonding material 16 may alternatively be initially flowed in the bonding features 24A, 24B of the main body 12 and/or placed on the engagement surface 20 of the main body 12 in a solidified state. The volume of the bonding material 16 can be greater than the volume of the bonding features 24A, 24B of the main body 12 and pores of the second porous layer 34 individually, and the volume of the bonding material 16 can be approximately equal to the combined volume of the bonding features 24A, 24B and pores of the second porous layer 34.

To bond the porous material 14 to the main body 12, for example, the bonding material 16 can be melted to a flowable state, placed between the porous material 14 and engagement surface 20, and the porous material 14 and engagement surface 20 can be compressed together so that the flowable bonding material 16 flows into the bonding features 24A, 24B and/or the pores of the second porous layer 34. As the porous materials 14A, 14B and the main body 12 are heated and/or pressed together, the bonding material 16 can at least partially fill the pores of each second porous layer 30 of the porous materials 14A, 14B and the bonding features 24A, 24B of the main body 12 in order to produce a solid bond. As can be seen in FIG. 5, the bonding material 16 can completely fill the grooves 26 of the main body 12 and the pores of each second porous layer 30 of the porous materials 14A, 14B. After flowing into the grooves 26 of the engagement surface 20 and pores of the second porous layer 34, the bonding material 16 can harden to form a solid material interface between the porous materials 14A, 14B and the implant body 12. When the bonding features 24A, 24B have different dimensions W1, W2 along the depth D, having the second region RB with the larger dimension W2 further in the depth D can cause the hardened bonding material 16 in the second region RB to resist being pulled through the first region RA with the smaller dimension W1. The resistance of the hardened bonding material 16 in the second region RB to pull out can allow the bonding of the porous materials 14A, 14B to the main body 12 to be relatively secure so the porous materials 14A, 14B are not easily detached from the main body 12 during and after implantation.

It should be appreciated that while the bonding material 16 is previously described as being melted to a flowable state, the bonding material 16 can be a chemically hardened material, e.g., a resin or epoxy, which starts in a flowable state and then hardens spontaneously or in the presence of a catalyst. If the bonding material 16 is a chemically hardened material, the bonding material 16 can have a first component placed in the pores of the second porous layer 34 and a second component placed in the bonding features 24A, 24B so that when the porous material 14 contacts the engagement surface 20 the first component and second component intermix and harden, forming a solid bonding material between the porous material 14 and the main body 12.

The bonding material 16 may initially be in the form of, for example, a solid, a high-viscosity liquid, or a thin film. The bonding material 16 can be solid at a normal body temperature, i.e. approximately 37-40° C., so the solidified bonding material 16 does not loosen while implanted. The bonding material 16 may be, for example, a biocompatible material such as PEEK or other body-temperature stable polymer. As shown, the bonding material 16 is initially in the form of a film 16 having a shape corresponding to the shape of the porous materials 14A, 14B. Additionally, the film 16 may partially or substantially cover the bonding features 24A, 24B of the main body 12 and/or the second porous layers 34 of the porous materials 14A, 14B. The film 16 may be positioned in between the porous material 14 and the main body 12. It should be appreciated that the orthopaedic implant 10 may include one or more bonding materials 16, for example, the bonding material 16 may include both a liquid adhesive and a film acting in conjunction to bond the porous material 14 and the main body 12.

Additionally, the bonding material 16 may be introduced by injection molding. For example, the bonding material 16 may be injected into the grooves 26 of the bonding features 24A, 24B first and then into the pores of the second porous layers 34 of the porous materials 14A, 14B. The bonding material 16 may be injected through one or more injection channel(s) that are connected to the grooves 26 of the bonding features 24A, 24B. As the porous materials 14A, 14B are held against the engagement surface 20, the bonding material 16 may be injected into the injection channel. Thereby, the bonding material 16 may be directly injected into the grooves 26 of the bonding features 24A, 24B. Once the grooves 26 become filled with the bonding material 16, further injection may force the bonding material 16 into the pores of the second porous layers 34 of the porous materials 14A, 14B. It is conceivable to select and adjust the temperature and/or flow rate of the injected bonding material 16 such that a desired amount of bonding material 16 may fill the grooves 26 and pores of the second layers 34. For example, the temperature and flow rate of the injected bonding material 16 can be high enough so that the bonding material 16 may flow into the grooves 26 and pores of the second porous layers 34 before the bonding material 16 begins to harden. Further, additional injection channels may be included at desired locations in order to obtain a desired amount of bonding material 16 that fills the grooves 26 and pores of the second porous layers 34 before the bonding material 16 begins to harden. It is also possible to select a bonding material 16 with a desired viscosity and various other characteristics such that a sufficient amount of bonding material 16 fills the grooves 26 and pores of the second porous layers 34 at a given temperature, flow rate, and/or number of injection channels. It should be appreciated that the injection molding of the bonding material 16 may occur in addition to applying pressure and/or thermal energy to the main body 12 and/or the porous materials 14A, 14B.

Figure 3:
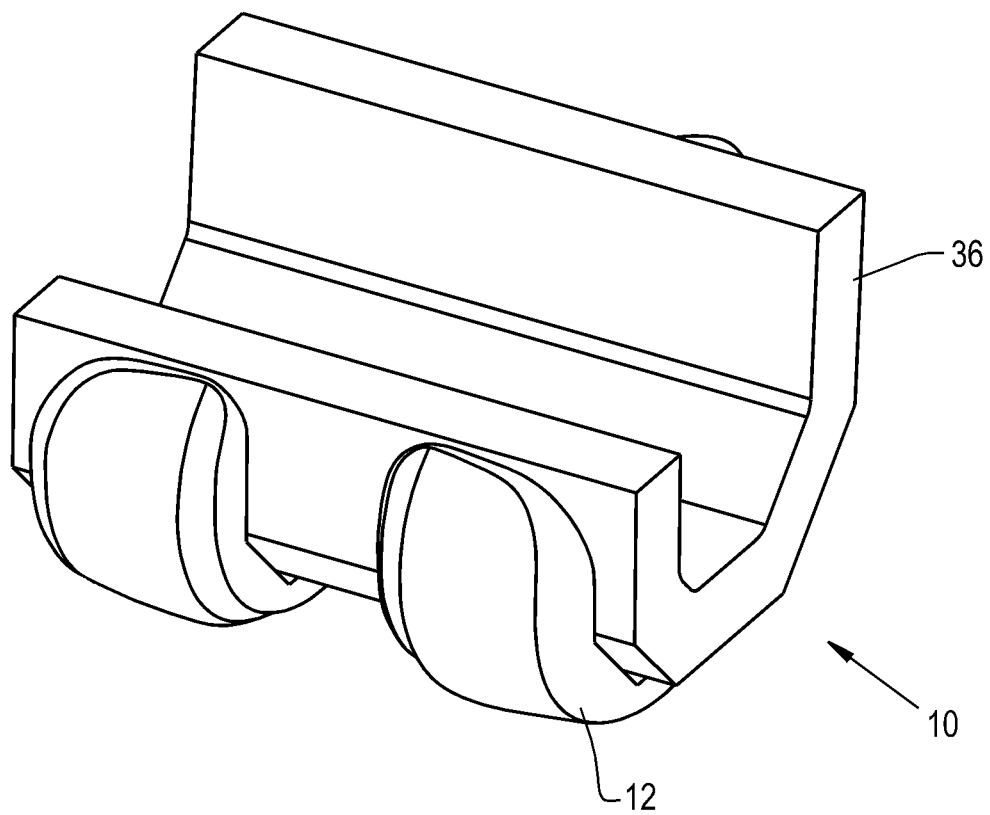
FIG. 3 is a perspective view of the orthopaedic implant of FIG. 2 combined with the induction heater of FIG. 2, in accordance with an embodiment of the present invention.

The main body 12 and porous materials 14A, 14B can be bonded together by pressing the main body 12 and porous materials 14A, 14B together and/or by applying thermal energy to the main body 12 and/or the porous materials 14A, 14B. An induction heater 36 may provide the requisite thermal energy to the porous materials 14A, 14B and/or to the main body 12 in order to melt the bonding material 16. The induction heater 36 is shown to have a "U" shape corresponding to the shape of the orthopaedic implant 10. However, the induction heater 36 may be in the form of any desired shape. As shown in FIGS. 2-4, the induction heater 36 directly contacts the first porous layers 30 of the porous materials 14A, 14B. The induction heater 36 may, however, only partially contact the porous materials 14A, 14B, or the induction heater 36 may be configured to not contact the porous materials 14A, 14B and thereby only apply thermal energy to the main body 12 and/or bonding material 16. Additionally, thermal energy may be applied in numerous other ways including pre-heating the bonding material 16, pre-heating the main body 12 to melt the bonding material 16 before pressing the porous materials 14A, 14B onto the main body 12, and/or preheating the porous materials 14A, 14B. Once the bonding material 16 has been flowed into the pores of the second porous layer 34 and the bonding features 24A, 24B, the induction heater 36 can be removed and thereby the application of thermal energy can be ceased to allow the bonding material 16 to harden.

As previously described, the porous materials 14A, 14B can include a non-porous layer 32 sandwiched between the first porous layer 30 and the second porous layer 34. During bonding of the porous materials 14A, 14B to the main body 12, the bonding material 16 flows into the pores of the second porous layer 34. If the first porous layer 30 and second porous layer 34 were in fluid communication with one another, the bonding material 16 could possibly flow into the first porous layer 30 while flowing into the second porous layer 34. Flowing the bonding material 16 into the first porous layer 30 could reduce the amount of tissue ingrowth into the first porous layer 30, reducing the ability of the implant 10 to fixate following implantation, and also push out bioactive substances held within the pores of the first porous layer 30. The non-porous layer 32, therefore, can act as a material barrier between the first porous layer 30 and the second porous layer 34 so the bonding material 16 cannot flow into the pores of the first porous layer 30 while flowing into the pores of the second porous layer 34. The non-porous layer 32 can also act as a tissue ingrowth barrier, so tissue ingrowth into the first porous layer 30 does not extend into the second porous layer 34 and create an excessive amount of fixation between the implant 10 and the implantation site.

The method of bonding the main body 12 and the porous materials 14A, 14B includes providing the main body 12 of the orthopaedic implant 10 and the porous material 14. The porous materials 14A, 14B are placed against the bonding features 24A, 24B. The bonding material 16 may be melted between the porous materials 14A, 14B and the bonding features 24A, 24B on the engagement surface 20 to a flowable state. The flowable bonding material 16 can be flowed into the pores of the second porous layers 34 of the porous materials 14A, 14B and the bonding features 24A, 24B of the engagement surface 20 by compressing the porous material 14 and main body 12 in order to bond the porous materials 14A, 14B to the main body 12. The method can also include hardening the bonding material 16 by, for example, cooling to bond the main body 12 and the porous materials 14A, 14B together.

By including a bonding material 16 and applying pressure and/or thermal energy according to an exemplary embodiment of the present invention, the process of bonding the porous materials 14A, 14B to the main body 12 may be precisely controlled. Thereby, the effects on the pores and the thermal distortion of the porous material 14 may be reduced during the bonding process and a stable, long-lasting bond can be formed.

It should be appreciated that the heating method may be varied depending upon the material chosen for different components. For example, thermal energy may not be applied through the porous material 14 if the porous material 14 is a polymer with a relatively low melting point, since the applied thermal energy may melt the porous material 14, occluding or destroying pores of the porous material 14; instead, thermal energy may be applied to the main body 12. Further, the duration and rate of applying thermal energy may also be varied depending upon the materials and characteristics of the various components chosen. Further, to reduce the possibility of deformation of the pores of the first porous layer 30, the porous materials 14A, 14B may be pressed to the engagement surface 20 of the main body 12 by applying pressure to the non-porous layer 32 and/or the second porous layer 34.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An orthopaedic implant, comprising:
   a main body having a surface with at least one bonding feature;
   at least one porous material having a plurality of pores; and
   a bonding material placed in said plurality of pores of said at least one porous material and said at least one bonding feature to form a bond between said at least one porous material and said main body, wherein the at least one bonding feature is formed to a depth D in the surface, and wherein a width W of the at least one bonding feature closer to the surface is less than a width of the at least one bonding feature further from the surface.

2. The orthopaedic implant of claim 1, wherein the at least one bonding feature includes a plurality of at least one of grooves, slots, and bores configured to receive the bonding material.

3. The orthopaedic implant of claim 1, wherein the at least one bonding feature includes a plurality of grooves, said plurality of grooves including a first pattern of grooves and a second pattern of grooves.

4. The orthopaedic implant of claim 3, wherein the first and second pattern of grooves form a sinusoidal pattern.

5. The orthopaedic implant of claim 1, wherein the at least one porous material includes one or more first porous layers defining an outer surface of said at least one porous material, one or more second porous layers having said plurality of pores, and a non-porous layer positioned between the one or more first porous layers and the one or more second porous layers.

6. The orthopaedic implant of claim 5, wherein said one or more first porous layers are formed of porous ingrowth material, said porous ingrowth material having a second plurality of pores configured to interface with bone material.

7. The orthopaedic implant of claim 6, wherein said second plurality of pores include one or more bioactive substances.

8. The orthopaedic implant of claim 5, wherein said one or more first porous layers include two or more first porous layers bonded to one another, each first porous layer of said two or more first porous layers having a pore pattern.

9. The orthopaedic implant of claim 1, wherein said surface of said main body is configured for engaging a resected femur.

10. The orthopaedic implant of claim 9, wherein said main body has an articulating surface opposite said surface, said articulating surface configured for articulating against a head of a tibia.

11. The orthopaedic implant of claim 10, wherein said main body is shaped for a femoral knee implant.

12. A method of forming an orthopaedic implant, comprising:
    providing an implant including a main body having a surface with at least one bonding feature;
    placing a porous material against said surface, said porous material having a plurality of pores; and
    flowing a bonding material into said at least one bonding feature and said plurality of pores to bond the porous material to the implant, wherein the at least one bonding feature is formed to a depth D in the surface, and wherein a width W of the at least one bonding feature closer to the surface is less than a width of the at least one bonding feature further from the surface.

13. The method according to claim 12, wherein said flowing includes melting said bonding material and pressing said porous material against said surface to force said melted bonding material into at least one of said plurality of pores and said at least one bonding feature.

14. The method according to claim 12, further comprising hardening said bonding material in said at least one bonding feature and said plurality of pores.

15. The method according to claim 12, wherein said bonding material comprises two flowable components that form a solid bond upon being mixed together, wherein flowing said bonding material further comprises flowing a first component of said bonding material into said at least one bonding feature and flowing a second component of said bonding material into said plurality of pores to bond the porous material to the implant.

16. The method according to claim 12, wherein the at least one bonding feature includes a plurality grooves, and wherein flowing said bonding material further comprises injecting said bonding material into said plurality of grooves for initially filling said plurality of grooves and subsequently filling said plurality of pores.

17. The method according to claim 12, wherein said porous material includes one or more first porous layers defining an outer surface of said porous material, one or more second porous layers having said plurality of pores, and a non-porous layer positioned between the one or more first porous layers and the one or more second porous layers.

18. The method according to claim 17, wherein said one or more first porous layers are formed of porous ingrowth material, said porous ingrowth material having a second plurality of pores configured to interface with bone material.

19. An orthopaedic implant, comprising:
a main body having a surface with at least one bonding feature;
at least one porous material having a plurality of pores; and
a bonding material placed in said plurality of pores of said at least one porous material and said at least one bonding feature to form a bond between said at least one porous material and said main body, wherein the at least one bonding feature includes a plurality of grooves, said plurality of grooves including a first pattern of grooves and a second pattern of grooves, wherein the first and second pattern of grooves form a sinusoidal pattern.

20. An orthopaedic implant, comprising:
a main body having a surface with at least one bonding feature;
at least one porous material having a plurality of pores; and
a bonding material placed in said plurality of pores of said at least one porous material and said at least one bonding feature to form a bond between said at least one porous material and said main body, wherein the at least one porous material includes one or more first porous layers defining an outer surface of said at least one porous material, one or more second porous layers having said plurality of pores, and a non-porous layer positioned between the one or more first porous layers and the one or more second porous layers.

* * * * *